(12) United States Patent
Jacob et al.

(10) Patent No.: US 10,370,254 B2
(45) Date of Patent: Aug. 6, 2019

(54) METHOD FOR PRODUCING BORAZANE

(71) Applicants: AIRBUS SAFRAN LAUNCHERS SAS, Issy-les-Moulineaux (FR); CENTRE NATIONAL DE LA RECHERCHE SCIENTIFIQUE, Paris (FR); UNIVERSITE CLAUDE BERNARD LYON I, Villeurbanne (FR)

(72) Inventors: Guy M. Jacob, Vert le Petit (FR); Henri R. Delalu, Lyons (FR); Ahmad A. El Hajj, Villeurbanne (FR)

(73) Assignees: AIRBUS SAFRAN LAUNCHERS SAS, Issy-les-Moulineaux (FR); CENTRE NATIONAL DE LA RECHERCHE SCIENTIFIQUE, Paris (FR); UNIVERSITE CLAUDE BERNARD LYON I, Villeurbanne (FR)

( * ) Notice: Subject to any disclaimer, the term of this patent is extended or adjusted under 35 U.S.C. 154(b) by 255 days.

(21) Appl. No.: 15/313,287

(22) PCT Filed: May 22, 2015

(86) PCT No.: PCT/FR2015/051360
§ 371 (c)(1),
(2) Date: Nov. 22, 2016

(87) PCT Pub. No.: WO2015/177483
PCT Pub. Date: Nov. 26, 2015

(65) Prior Publication Data
US 2017/0305750 A1      Oct. 26, 2017

(30) Foreign Application Priority Data

May 23, 2014   (FR) ...................... 14 54695

(51) Int. Cl.
*C01B 35/14*        (2006.01)
*C07F 5/02*         (2006.01)

(52) U.S. Cl.
CPC ............ *C01B 35/146* (2013.01); *C01B 35/14* (2013.01); *C07F 5/022* (2013.01)

(58) Field of Classification Search
CPC ........ C01B 35/14; C01B 35/146; C07F 5/022
See application file for complete search history.

(56) References Cited

U.S. PATENT DOCUMENTS

| 3,296,144 A | 1/1967 | White |
| 5,481,038 A | 1/1996 | Brown |

(Continued)

FOREIGN PATENT DOCUMENTS

| WO | WO 2007/120511 A2 | 10/2007 |
| WO | WO 2010/123985 A1 | 10/2010 |

OTHER PUBLICATIONS

International Search Report as issued in International Patent Application No. PCT/FR2015/051360, dated Aug. 14, 2015.

(Continued)

*Primary Examiner* — Amber R Orlando
*Assistant Examiner* — Syed T Iqbal
(74) *Attorney, Agent, or Firm* — Pillsbury Winthrop Shaw Pittman LLP

(57) ABSTRACT

A process for obtaining borazane ($NH_3$—$BH_3$) includes introducing anhydrous liquid ammonia ($NH_3(l)$) into a reactor thermostatically regulated to between a temperature $\theta_1$ and 40° C.; introducing, with stirring, into the reactor an amine borane complex ($Am.BH_3$), the corresponding amine (Am) of which is soluble in anhydrous liquid ammonia only to a proportion of less than 10 g in 100 g of ammonia at 20° C., being introduced in an amount such that the mole ratio $R = (NH_3(l))/(Am.BH_3)$ is greater than or equal to 5; stirring (Continued)

the mixture; stopping the stirring to obtain two demixed phases: a light phase constituted essentially of a solution of anhydrous liquid ammonia ($NH_3(l)$) containing borazane; and a heavy phase constituted essentially of the amine corresponding to the amine borane complex introduced; isolating the borazane and drying under vacuum thereof; the temperature $\theta_1$ being greater than or equal to the melting point of the amine borane complex.

20 Claims, 2 Drawing Sheets

(56) References Cited

U.S. PATENT DOCUMENTS

| | | | |
|---|---|---|---|
| 7,977,508 B2* | 7/2011 | Shore | C01B 35/14 |
| | | | 544/106 |
| 2010/0272623 A1* | 10/2010 | Lukacs, III | C01B 35/14 |
| | | | 423/285 |
| 2013/0121905 A1* | 5/2013 | Goudon | C01B 35/08 |
| | | | 423/285 |

OTHER PUBLICATIONS

Shore, S.G., et al., "The Crystalline Compound Ammonia-Borane, $H_2NBH_2$," J. Am. Chem. Soc., 1955, vol. 77, pp. 6084-6085.
Shore, S.G., et al., "Large Scale Synthesis of $H_2B(NH_3)_2{}^+BH_4{}^-$ and $H_3NBH_2$," Inorg. Chem., 1964, vol. 3, pp. 914-915.
Mayer, E., "Conversion of Dihydridodiammineboron(III) Borohydride to Ammonia-Borane without Hydrogen Evolution," Inorg. Chem., 1973, vol. 12, pp. 1954-1955.

* cited by examiner

METHOD FOR PRODUCING BORAZANE

CROSS REFERENCE TO RELATED APPLICATIONS

This application is the U.S. National Stage of PCT/FR2015/051360 filed May 22, 2015, which in turn claims priority to French Application No. 1454695 filed May 23, 2014. The contents of both applications are incorporated herein by reference in their entirety.

The present invention relates to a process for synthesizing (or process for obtaining) borazane or ammonia borane of chemical formula $NH_3BH_3$. This process, which makes it possible to obtain a product of high purity, is particularly advantageous as a result of an implementation, without organic solvent, "at room temperature", and with possible recycling, especially that of the coproduct formed.

The synthesis of borazane is a key for the success of programs for generating hydrogen from solid compounds. This generation of hydrogen from solid compounds is currently one of the means proposed for feeding fuel cells. In this context, is already known the use of borazane (or ammonia borane) as a solid precursor for hydrogen production.

In point of fact, the borazane or ammonia borane complex, of chemical formula $NH_3BH_3$, which exists in the form of a white crystalline powder, has the unique potential of containing 19.6% by mass of hydrogen. It is thus positioned as a particularly advantageous candidate for the solid storage of hydrogen.

At the present time, to the inventors' knowledge, no process for synthesizing borazane which is suitable for its industrial-scale manufacture has as yet been proposed. Various approaches have, however, been studied, or even developed.

The standard processes for synthesizing borazane ($NH_3BH_3$) comprise the reaction of at least one ammonium salt (generally chosen from ammonium chloride, ammonium sulfate, ammonium carbonate, ammonium formate and mixtures thereof) with at least one alkali metal and/or alkaline-earth metal borohydride (generally chosen from lithium borohydride, sodium borohydride and mixtures thereof), in a solvent, preferably tetrahydrofuran (THF). They are widely described in the literature, and have been described for a long time. (see S. G. Shore and R. W. Parry, J. Am. Chem. Soc., 1955, 77, pages 6084-6085). The reaction is generally performed between such an ammonium salt and such a borohydride. The process most commonly used consists in reacting ammonium carbonate $(NH_4)_2CO_3$ with sodium borohydride $NaBH_4$, in THF. The $NH_3BH_3$ formed is soluble in said THF. It is separated from the sodium carbonate that is also formed, which precipitates out. Specifically, at the end of the reaction, the THF solution (thus containing $NH_3BH_3$ in solution) is filtered to remove therefrom the majority of the solids in suspension. The THF solvent is then evaporated off. A powder is finally recovered, which essentially contains the desired complex (borazane or ammonia borane). These conventional processes require the use of a very anhydrous solvent, such as THF, so as to avoid the production of byproducts, most particularly that of boron oxides, and are performed in relatively unconcentrated media (due to the relatively low solubility of the reagents in the solvent), which leads, for a large-scale production, to substantial solvent reprocessing costs.

The ammonolysis of diborane ($B_2H_6$), using liquid ammonia, does not make it possible to obtain borazane directly. Performed at low temperature, generally at temperatures in the region of −78° C., it rather produces diborane diammoniate ($[(NH_3)_2BH_2]^+[BH_4]^-$). The formation of borazane, from said diborane diammoniate, is then performed by heating said diborane diammoniate in an organic solvent, preferentially an ether, containing traces of diborane, at room temperature, as shown in the reaction scheme below (see, for example, Shore, S G; Böddeker, K W in Inorg Chem 1964, 3, 914, and Mayer, E. in Inorg Chem, 1973, 12, 1954):

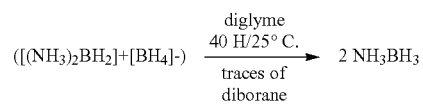

This process, comprising a first reaction at low temperature and a second reaction in the presence of a solvent, is thus difficult to implement.

Patent application WO 2007/120 511 describes a process for synthesizing ammonia borane, comprising the reaction of at least one amine borane with gaseous ammonia, said amine borane being chosen from aniline boranes, such as dimethylaniline borane and diethylaniline borane, phenylmorpholine boranes and pyridine boranes, such as lutidine. At least one of said amine boranes is reacted with ammonia, thus introduced in gaseous form, advantageously by bubbling in a solvent containing said at least one amine borane in solution. Such a solvent is especially chosen from toluene, heptane, xylenes and mixtures thereof. In reference to the reaction yield, the reagent gaseous ammonia is not introduced in excess (its introduction is stopped once the amine borane has been consumed: see the examples of said patent application WO 2007/120 511) due to the solubility of the ammonia borane formed in the solvent/gaseous ammonia "mixtures". The separation, at the end of the reaction, of the ammonia borane formed, from the (unreacted) amine and the solvent, is performed, for example, by filtration. Such a separation does not in principle ensure a very high degree of purity of said ammonia borane formed. In any case, with reference to the purity of said ammonia borane formed, the removal of the solvent used should undoubtedly be optimized. The Applicant evaluated this process (by reacting diethylaniline borane, dissolved in toluene, with gaseous ammonia (introduced in stoichiometric amounts); said gaseous ammonia being bubbled into the solution). It was unable to obtain a synthetic yield of more than 50% (by mass). Moreover, the ammonia borane obtained did not have the purity required for use in a fuel cell. It was contaminated with solvent (toluene); efficient removal of said solvent, by heat treatment, being difficult to perform at temperatures that are compatible with the stability of said ammonia borane.

Patent application WO 2010/123 985 describes a process for preparing ammonia borane from a compound containing boron in its chemical formula, which is capable of reacting under pressure with liquid ammonia to form said ammonia borane. Said process, described in very general terms, comprises the following steps:
- constituting a reaction mixture in a reactor, said reaction mixture comprising anhydrous liquid ammonia and said compound containing boron in its chemical formula, which is capable of reacting under pressure with liquid ammonia to form ammonia borane; and
- heating said reaction mixture, from a first temperature of greater than or equal to −33° C. up to a second temperature, under pressure, to form ammonia borane.

Said compound containing boron in its chemical formula may be chosen from a very long list especially comprising ammonium borohydride, diborane and alkyl amine boranes (especially tert-butylamine borane and triethylamine borane). An organic solvent, such as an ether, chosen especially from the group consisting of tetrahydrofuran, glyme, diglyme, triglyme, diethyl ether, dibutyl ether, methyl ethyl ether, diethoxyethane and mixtures thereof, Is advantageously present in the reaction medium.

According to one embodiment variant, an ammonium borohydride, generated in situ from an ammonium salt and a borohydride in anhydrous liquid ammonia (the solubility of the reagents in said anhydrous liquid ammonia is greater than the solubility of said reagents in an ether, such as THF (see above)), is decomposed in a solvent medium containing said liquid anhydrous ammonia and an ether. On conclusion of the reaction, said ammonia and ether must successively be removed.

According to another embodiment variant, a borane-THF complex is reacted with anhydrous liquid ammonia at a temperature of between 4° C. and 7° C. On conclusion of the reaction, the unreacted liquid ammonia and the THF (released from the complex) should be removed.

In general, the processes of the prior art thus include a step (for example of evaporation) to remove an organic solvent which needed to be manipulated upstream (as solvent for the reagent(s) or as constituent element of a reagent). The intervention of such a solvent makes the implementation of said processes, most particularly on an industrial scale, complex and increases the cost price of the desired product (borazane or ammonia borane).

The prior art does not, at the present time, propose a simple, readily industrializable implementation process for directly obtaining ammonia borane that can be used as a solid source of hydrogen (i.e. having a degree of purity such that, in principle, it makes any additional purification step superfluous).

A person skilled in the art knows that ammonia borane must not contain any impurities (traces of solvent and/or of other carbon-based products, etc.) liable to generate, during the use of said ammonia borane as a solid source of hydrogen in a fuel cell, poisons that are prohibitive to the cell, and especially CO (at the present time, the fuel cells that are the most tolerant from this point of view do not withstand more than 3% by mass of CO). As regards the impurities that are not liable to generate a poison for the cell (for example boron oxides (see below)), they are detrimental with regard to the yield of ammonia borane (during its production) and thus also with regard to the yield of hydrogen (during the use of said ammonia borane).

The present invention proposes a simple, readily industrializable implementation process for directly obtaining ammonia borane that can be used as a solid source of hydrogen.

One subject of the present invention is a process for obtaining borazane ($NH_3$—$BH_3$), which is novel and particularly advantageous. This process comprises:
providing a reactor, equipped with stirring means and thermostatically regulated at a temperature between a temperature $\theta_1$ and 40° C.;
introducing anhydrous liquid ammonia into said reactor;
introducing, with stirring, into said reactor containing the anhydrous liquid ammonia, an amine borane complex, said amine borane complex, the corresponding amine of which is not soluble in anhydrous liquid ammonia (i.e. soluble to a proportion of less than 10 g per 100 g of anhydrous liquid ammonia, at a temperature of 20° C.), being introduced in an amount such that the mole ratio R=anhydrous liquid ammonia/amine borane complex is greater than or equal to 5;
stirring the mixture to the point of depletion of said amine borane complex;
stopping the stirring and obtaining, in said reactor, two demixed phases:
a light phase constituted essentially of a solution of anhydrous liquid ammonia containing borazane; and
a heavy phase constituted essentially of the amine corresponding to the amine borane complex introduced;
isolating said borazane and drying under vacuum thereof;
said temperature $\theta_1$ being greater than or equal to the melting point of said amine borane complex.

The synthesis of borazane according to the invention is performed in a reactor:
equipped with stirring means;
thermostatically regulated at a temperature between the temperature $\theta_1$ and 40° C. Said temperature must be sufficient ($\geq \theta_1$) for the amine borane complex to be liquid, but not excessive ($\leq 40°$ C.), most particularly with regard to the stability of borazane. The reaction is in fact advantageously performed at room temperature, i.e. at 20° C.;
which is obviously capable of containing the liquid ammonia reagent (anhydrous), i.e. which withstands pressure. A person skilled in the art understands that a low-pressure reactor is entirely suitable for use, in particular a glass or metal low-pressure reactor. It is obviously not excluded to use a high-pressure reactor. Generally, the anhydrous liquid ammonia is introduced at a pressure of between $5 \times 10^5$ to $10^6$ Pa (between 5 and 10 bar, limit values included), advantageously between $7 \times 10^5$ and $9 \times 10^5$ Pa (between 7 and 9 bar, limit values included).

According to an advantageous implementation variant of the process of the invention, the reactor is rendered inert prior to the introduction of the reagents (prior to the introduction of the anhydrous liquid ammonia). It may thus advantageously be rendered inert with nitrogen or argon. This inertizing is appropriate so as to minimize the spurious formation of byproducts, most particularly that of boron oxides (see also the intervention of anhydrous liquid ammonia) and thus to optimize the yield. However, it is not obligatory, since the byproducts concerned do not constitute poisons for fuel cells. Thus, the process of the invention may also be performed in the presence of air in the reactor. In such a case, about 10% by mass of boron oxides was generated.

The participating reagents are, successively:
said anhydrous liquid ammonia (which is anhydrous so as to minimize the spurious formation of byproducts, especially of boron oxides (see also above the inertizing of the reactor that is advantageously performed)). In the present text, the term "anhydrous" means containing less than 100 ppm of water; and
an amine borane complex. It is noted that the word "an" used herein should be understood as meaning "at least one". Specifically, it cannot be excluded from the scope of the invention for several amine borane complexes to be reacted with liquid ammonia. Generally, however, for better control of the reaction, a single amine borane complex is introduced into the reactor, for reaction with the liquid ammonia. The synthesis of amine borane complexes is described in the literature (see later); certain amine borane complexes are commercially available.

No solvent is necessary; no solvent is used.

The process of the invention thus in fact comprises:
providing anhydrous liquid ammonia,
providing an amine borane complex, the corresponding amine of which is not soluble in anhydrous liquid ammonia (i.e. soluble to a proportion of less than 10 g per 100 g of anhydrous liquid ammonia, at a temperature of 20° C.); said complex having a melting point $\theta_f$, and
providing a reactor, equipped with stirring means and thermostatically regulated at a temperature T between a temperature $\theta_1$ and 40° C. ($\theta_1 \leq T \leq 40°$ C.), said temperature $\theta_1$ being greater than or equal to the melting point $\theta_f$ of said amine borane complex; said temperature T thus being such that: $\theta_f \leq T \leq 40°$ C. (such that the reaction takes place between the liquid ammonia and the liquid amine borane complex and there is no stability problem for the borazane synthesized).

Said liquid ammonia is introduced first so that the reaction always proceeds in the presence of an excess of ammonia (see below).

The inventors have, to their merit, selected:
1) the reagents, i.e. a reaction of the type:
Am.BH$_3$+(liquid) NH$_3$ to give NH$_3$BH$_3$+Am (general equation 1); and also
2) the conditions for performing said reaction (anhydrous liquid ammonia, in which the amine (Am) is insoluble, being used in excess: see above+below)
which ensure a particularly advantageous result.

The inventors have, to their merit, selected a reaction:
whose implementation does not require any organic solvent (liable to contaminate the borazane synthesized),
which is complete (or virtually complete),
which (directly) generates two demixed phases, the one containing the desired borazane (dissolved in the (anhydrous) liquid ammonia) being separated from the one containing the amine (derived from the starting amine borane complex);
the borazane thus being able readily to be obtained in a degree of purity that is suitable for its use in a fuel cell.

To obtain said result, the conditions, concerning the reagents, A and B detailed below should be complied with, in addition to the conditions already mentioned above:

A) the complex Am.BH$_3$ is not an (at least one, see above) arbitrary Am.BH$_3$ complex; it comprises an amine (Am) that is insoluble in anhydrous liquid ammonia (containing less than 100 ppm of water (see above)) at the reaction implementation temperatures. This insolubility of the amine was quantified as follows: less than 10 g of the amine per 100 g of anhydrous liquid ammonia, at a temperature of 20° C. This insolubility is essential with regard to the demixing, with the presence of a minimum amount of amine, in liquid ammonia which contains the desired borazane, thus with regard to the purity of said desired borazane. This insolubility criterion sets aside the use, as amine borane complex reagent of the invention, especially of the N-tert-butylamine borane complex, the 4-methylmorpholine borane complex and the 4-ethylmorpholine borane complex.

Said amine borane complex may especially consist of an alkylamine borane complex, the amine of which is tertiary. Such an amine borane complex may be chosen from the N,N,N-triisopropylamine borane complex, the N,N-diisopropyl-N-ethylamine borane complex and mixtures thereof. It advantageously consists of the N,N-diisopropyl-N-ethyl-amine borane complex. The reaction performed according to the invention is then written as follows:

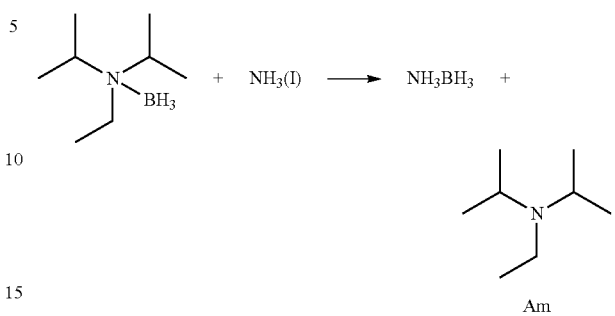

For all relevant purposes, the results of a solubility study of N,N-diisopropyl-N-ethylamine (Am) in anhydrous liquid ammonia (containing less than 100 ppm of water (see above)) is proposed below. Samples containing said amine, in anhydrous liquid ammonia, diluted to the appropriate proportions in THF, were analyzed by UV (ultraviolet spectrometry) and GC/MS (gas chromatography-mass spectrometry). The experimental results are reported in table 1 below.

TABLE 1

Solubility of N,N-diisopropyl-N-ethylamine in anhydrous liquid ammonia

| T (° C.) | Solubility (g) in 100 g of NH$_3$(l) |
|---|---|
| −10 | 2.51 |
| 0 | 3.03 |
| 11 | 5.29 |
| 20 | 8.34 | and

B) the reagents participate in a mole ratio, R=anhydrous liquid ammonia/amine borane complex, of greater than or equal to 5. The anhydrous liquid ammonia is thus present in excess. It is always present in excess, due to the order of introduction of the reagents into the reactor (see above). This excess is advantageous both:

α) for the desired (complete or virtually complete) reaction, i.e. the formation of borazane according to the general equation 1, and that, even though this reaction is an equilibrium. Said excess of ammonia always promotes the reaction toward the formation of borazane, and β) to limit, or even prevent, a reaction between the starting amine borane complex and the borazane obtained. This decomplexation reaction of said complex, demonstrated by the inventors, is written as follows:

Am.BH$_3$+NH$_3$BH$_3$→Am+H2+by products

As regards this mole ratio R≥5, the following may be added. Said mole ratio is generally between 5 and 20 (5≤R≤20), advantageously between 8 and 20 (8≤R≤20), very advantageously between 8 and 12 (8≤R≤12). According to a preferred variant, it is equal to 10. A high ratio R is advantageous with regard to the yield (see above), but it cannot be too high with regard to the reaction kinetics, which explains the ranges indicated above for the values of R. For all relevant purposes, table 2 below shows the influence of said ratio R on the reaction performed with the N,N-diisopropyl-N-ethylamine borane complex.

TABLE 2

Influence of R
(with Am•BH₃ = N,N-diisopropyl-N-ethylamine borane)

| R = mole ratio (NH₃/Am•BH₃) | NH₃ (mol) | Am•BH₃ (mol) | T (° C.) | P (bar) | Time (minutes) | Yield (degree of conversion) |
|---|---|---|---|---|---|---|
| 50 | 0.665 | 0.013 | 20 | 8.5 | 40 | 94 |
| 20 | 0.59 | 0.029 | 20 | 8.5 | 22 | 93 |
| 10 | 0.59 | 0.059 | 20 | 8.5 | 15 | 93 |
| 5 | 0.353 | 0.064 | 20 | 8.5 | 10 | 84 |

The influence of the reaction temperature was more particularly studied, for a mole ratio R=[NH₃(l)]/[Am.BH₃]=10, with Am=N,N-diisopropyl-N-ethylamine. With this amine borane complex, the reaction is advantageously performed in a reactor thermostatically regulated at a temperature of between 18° C. and 30° C. (limit values included), advantageously between 18° C. and 25° C. (limit values included), very advantageously at 20° C. The recommended conditions are: R=10, T=20° C. (see table 2 above).

The two conditions (A and B) explained above—insolubility of the amine (Am) in anhydrous liquid ammonia and anhydrous liquid ammonia in excess—may, a posteriori, and only a posteriori, appear to be imposed. It was, in point of fact, not at all obvious to be able to control all of the parameters (temperature, pressure, kinetics, etc.) of the process of the invention.

The reaction, with the reagents identified above (suitable amine borane complex and anhydrous liquid ammonia), under the conditions specified above (excess of said ammonia (R≥5)), is performed to the point of depletion of the amine borane complex introduced, this with regard to its yield and to the purity of the borazane produced. Specifically, unreacted amine borazane complex would be responsible 1) for an unoptimized yield and 2) for contamination of the borazane produced (see below). The notion of depletion is quantified as follows: on conclusion of the reaction, said ("depleted") complex is no longer detectable by NMR (i.e. said complex is not able to be present in a content above 1% by mass). Given the excess ammonia used, this depletion is only a question of time. Thus, the stirring of the mixture introduced into the reactor is performed for the time required for depletion of the complex introduced. This required time obviously depends on the reaction kinetics at the temperature at which said reaction is performed. It is generally from 10 min to 120 min.

On stopping the stirring, the reaction medium (which has reacted for a sufficient time (predetermined by prior experiments or entirely manageable by sample analysis)) has the two phases identified above and specified below:
a light phase constituted essentially of a solution of anhydrous liquid ammonia containing borazane (the solubility of NH₃BH₃ in NH₃(l) is about 33 g in 100 g at 20° C.) (said light phase is generally constituted to more than 90% by mass of said solution of anhydrous liquid ammonia containing borazane. It thus generally contains less than 10% by mass of undesired product(s): dissolved amine (Am), essentially+boron oxides+(unreacted) amine borane complex, in trace amount only (less than 1% by mass (see above)); and
a heavy phase constituted essentially of the amine (Am) corresponding to the amine borane complex introduced (said heavy phase is generally constituted to more than 94% by mass of said amine. It generally contains from 2% to 6% of undesired product(s): amine degradation product(s), essentially).

The process of the invention therefore does not involve any organic solvent (which is particularly advantageous with regard to its ease of implementation and with regard to the purity of the borazane obtained). It generates borazane dissolved in anhydrous liquid ammonia, said solution (constituting the light phase of the obtained demixture) containing a small amount of amine (Am) (fixed by the low solubility (less than 10 g per 100 g) of said amine in said anhydrous liquid ammonia). The borazane obtained, once isolated (from said light phase), is dried under vacuum, to be freed of any contamination originating from said small amine content of the light phase. This drying under vacuum is efficient at temperatures that are entirely compatible with the stability of borazane. A person skilled in the art understands that this drying operation under vacuum is a much lighter operation than the operations required according to the prior art for removing the solvents used.

To isolate the borazane, the heavy phase should be removed, on the one hand, and the anhydrous liquid ammonia (of the light phase) should be removed, on the other hand. The process may especially be performed according to one or other of the two procedures specified below:
procedure A: after obtaining, in the reactor, the two demixed heavy and light phases, the following are performed:
discharging said heavy phase, constituted essentially of said at least one amine;
removing, by evaporation (following depressurization of the reactor), the anhydrous liquid ammonia of said light phase remaining in said reactor; and then
suction filtrating the solid (borazane) obtained (the amine recovered during the implementation of said suction filtration (conventional suction filtration by filtration under vacuum) is conveniently added to the discharged heavy phase).

The borazane thus isolated (contaminated with traces of amine) is then dried under vacuum.
procedure B: after obtaining, in the reactor, the two demixed heavy and light phases, the following are performed:
removing, by evaporation (following depressurization of the reactor), the anhydrous liquid ammonia of said light phase, lying on said heavy phase; and then
filtrating the (solid/liquid) mixture which results from said removal: borazane/heavy phase (in point of fact, heavy phase+amine which was dissolved in the light phase) mixture. Said filtration is advantageously performed under inert gas (especially nitrogen), with a view, in this case also, to minimizing or even preventing the formation of boron oxides.

The borazane is thus isolated from the heavy phase. The borazane thus isolated (contaminated with traces of amine) is then dried under vacuum.

Procedure B is preferred.

It was not obvious that a (virtually) complete reaction could be performed, "at room temperature", without resorting to an organic solvent and moreover that it would readily lead to borazane of desired purity (≥95% (by mass)). In this respect, the process of the invention is particularly efficient. What is more, said process can be performed with recycling, upstream, of the ammonia of the light phase and/or, advantageously and, of the heavy phase (Am) (see below).

Irrespective of the exact procedure used for recovering the borazane formed, it advantageously comprises recovering and upgrading of the ammonia removed by evaporation (gaseous ammonia). Said ammonia (gaseous) recovered may thus be recompressed (liquid-ammonia) and advantageously recycled (liquid) into the reactor.

Irrespective of the exact procedure used for recovering the borazane formed, it advantageously comprises recovering and upgrading of the amine (heavy phase (a minima) (discharged heavy phase+advantageously amine recovered on suction filtration (procedure A above) or heavy phase+amine dissolved in the light phase (procedure B above)). This upgrading preferably falls within a context of synthesis of the amine borane complex from diborane ($B_2H_6$) and an amine (Am), performed upstream of the reaction of said complex with anhydrous liquid ammonia. This synthesis was especially described in U.S. Pat. Nos. 3,296,144 and 5,481,038.

The process of the invention may in fact comprise, upstream of the reaction of the amine borane complex ($Am.BH_3$) with anhydrous liquid ammonia ($NH_3(l)$), synthesis of said amine borane complex from diborane ($B_2H_6$) and at least one amine (Am). For the implementation of this synthesis, which is then coupled to said reaction, the recovered amine is advantageously used.

The process for obtaining borazane of the invention, according to the reaction: $Am.BH_3+NH_3(l) \rightarrow NH_3BH_3+Am$, is thus advantageously coupled to the synthesis of the $Am.BH_3$ complex ($B_2H_6+Am \rightarrow :Am.BH_3$) and performed with recycling of the amine Am (i.e. with recycling of the coproduct formed).

A person skilled in, the art has already understood the full advantage of the invention.

Said invention is now described, in an entirely unlimiting manner, with reference to the attached figures and illustrated by the two examples below.

Said figures illustrate two implementation variants of the process of the invention.

Figure 1:
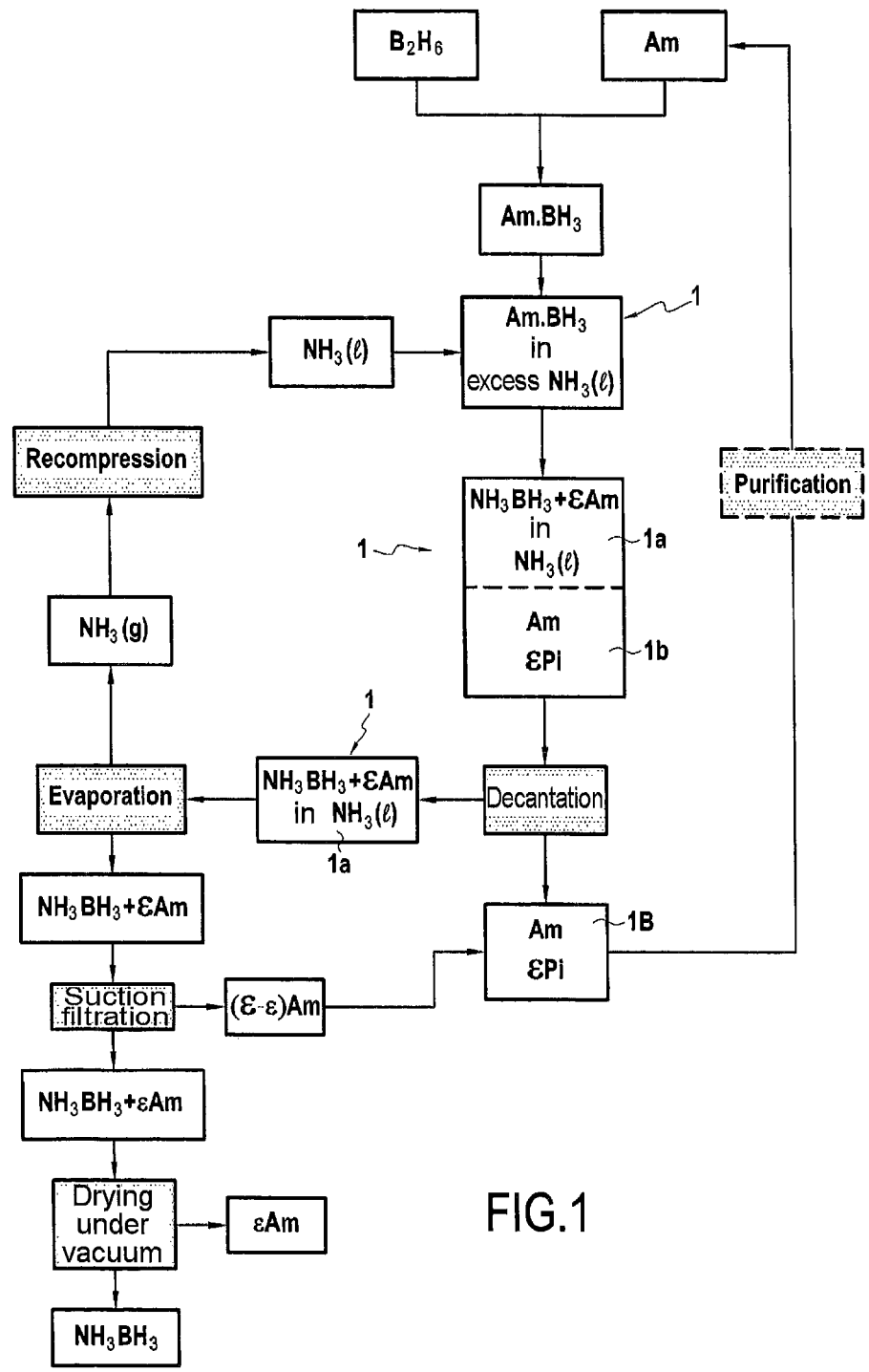
FIG. 1 is a flow chart of an implementation variant of the process of the Invention in which the borazane formed is recovered after discharge of the heavy phase (procedure A above)
Figure 2:
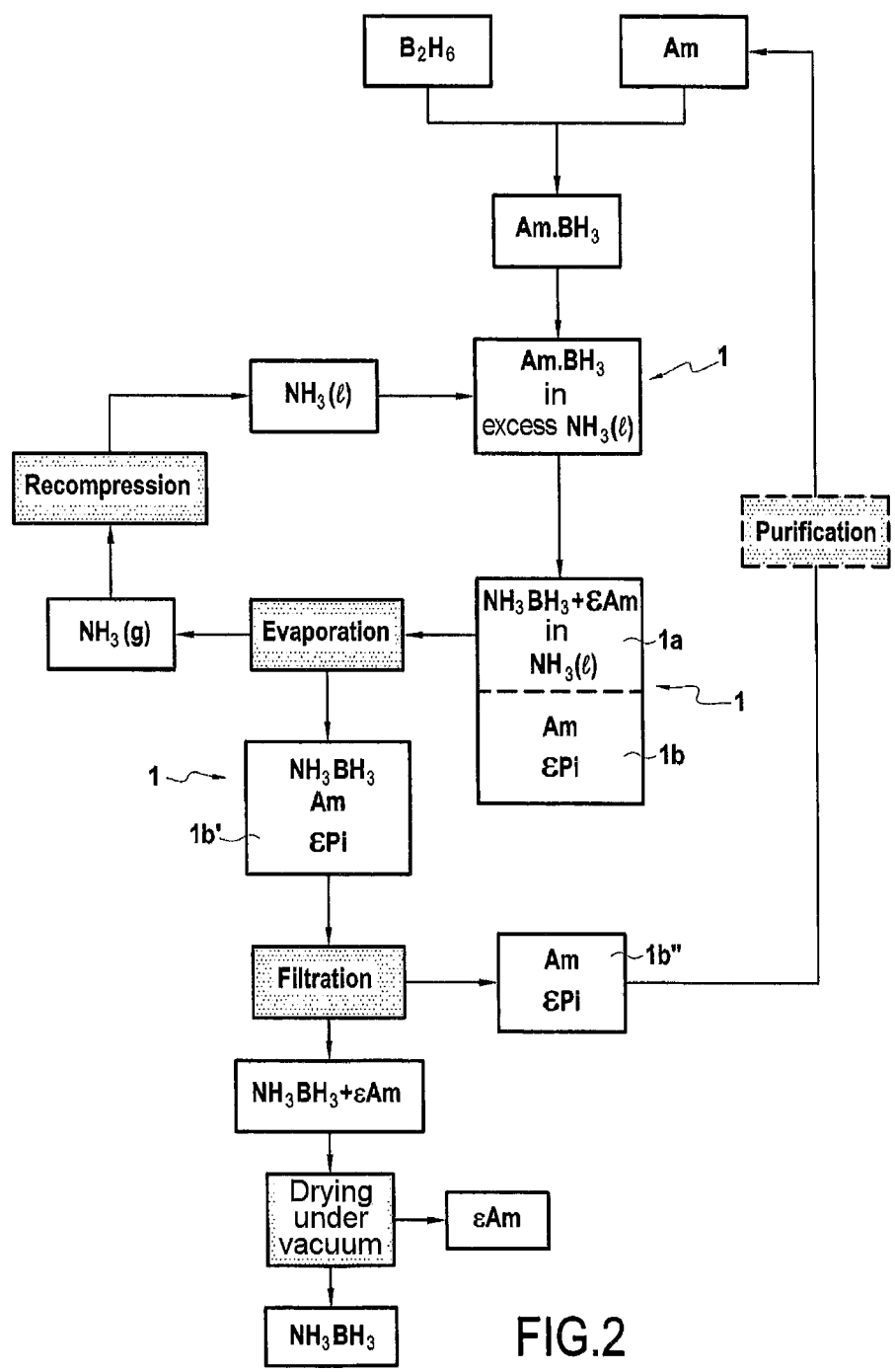
FIG. 2 is a flow chart of an implementation variant of the process of the invention in which the borazane formed is recovered after being mixed into the heavy phase (procedure B above).

In FIGS. 1 and 2, the synthesis of the $Am.BH_3$ complex is performed, upstream, from diborane ($B_2H_6$) and an amine (Am).

After introducing anhydrous liquid ammonia $NH_3(l)$ into reactor 1, the $Am.BH_3$ complex synthesized upstream is introduced therein and reacted.

On conclusion of the reaction, the following are found, demixed, in said reactor 1:
  a light phase 1a, lying on a heavy phase 1b, said light phase 1a essentially containing the borazane formed ($NH_3BH_3$) dissolved in the anhydrous liquid ammonia $NH_3(l)$ but also amine ($\varepsilon Am$) dissolved in said anhydrous liquid ammonia $NH_3(l)$;
  said heavy phase 1b essentially containing the amine (Am).

The presence, in small amounts, in said heavy phase 1b, of other products: $\varepsilon Pi$ (essentially products of decomposition of said amine (Am)) has been indicated.

According to the procedure represented schematically in FIG. 1, the heavy phase 1b is discharged. The borazane formed is then isolated as follows: 1) reactor 1 is depressurized, for evaporation of the ammonia, and 2) the borazane obtained, contaminated with amine ($\varepsilon Am$) is suction filtered by filtration under vacuum (it is thus, without impairment, virtually freed of the amine and the amine recovered is conveniently added to the heavy phase discharged). The borazane thus isolated is then contaminated only with traces of amine ($\varepsilon Am$). It has been schematically shown that these traces are in very limited amounts ($\varepsilon Am<\varepsilon Am$). Said isolated borazane is finally dried under vacuum.

According to the procedure represented schematically in FIG. 2, reactor 1 is first depressurized. The ammonia is evaporated off and the borazane is found in solid form in the heavy phase 1b. It in fact is constituted by a solid/liquid mixture, which, besides said heavy phase 1b, thus contains said borazane and amine ($\varepsilon Am$) originating from the light phase 1a. This mixture is referenced 1b'. For reasons of simplification, Am ($=Am+\varepsilon Am$) has been indicated. Filtration (advantageously under an inert gas) is then performed for isolation of said borazane. The isolated borazane is dried under vacuum to be freed (without impairment) of the traces of amine ($\varepsilon Am$) entrained on filtration. It has been schematically shown that these traces are in very limited amounts ($\varepsilon Am<\varepsilon Am$).

The heavy phase finally recovered (referenced 1B ($=1b+(\varepsilon-\varepsilon)Am$) in FIG. 1 and referenced 1b" ($=1b+(\varepsilon-\varepsilon)Am$) in FIG. 2; said figures obviously being considered independently) is, according to the two procedures represented schematically, recycled for the upstream synthesis of the $Am.BH_3$ complex. During this recycling, it is optionally (whence the dotted lines) purified. This optional purification may especially be performed by distillation. This purification is mainly directed toward removing the decomposition products of the amine Am ($\varepsilon Pi$, present, in more or less large amounts, depending on the operating temperature of the reaction).

The gaseous ammonia recovered is, according to the two procedures represented schematically, recompressed and used, in liquid form, to feed reactor 1.

EXAMPLE 1

A jacketed glass reactor, with a volume of 300 ml, withstanding a pressure of $10^6$ Pa (10 bar), equipped with a magnetic stirrer, was used.

It was rendered inert beforehand with nitrogen and thermostatically regulated at 20° C.

0.59 mol of ammonia was transferred, from an ammonia bottle (under $7 \times 10^5$ to $8 \times 10^5$ Pa (7 to 8 bar of pressure)) into said inertized and thermostatically regulated reactor.

Stirring was then started. The amine-borane complex (N,N-diisopropyl-N-ethylamine borane (commercial product); 0.059 mol) was then added in less than 30 seconds. The ammonia (liquid)/amine borane complex mole ratio was thus equal to 10.

After 15 minutes, the stirring was stopped. To check that the reaction (N,N-diisopropyl-N-ethylamine borane+$NH_3$ (liquid)) was complete, a sample of the reaction medium (liquid) was taken. The sampling (in a vial) was performed, hermetically, after placing the headspace of the internal volume of the reactor under nitrogen pressure. The sample withdrawn, diluted in tetrahydrofuran (THF), was analyzed by $^{11}B$ (boron) NMR. Absence of the amine-borane complex was confirmed. The reaction was thus complete (within the detection limits of the NMR analysis).

After stopping the stirring, the reaction medium was demixed and two phases were observed: a light phase, essentially containing the borazane ($NH_3BH_3$) formed in solution in the liquid ammonia, and a heavy phase essentially containing the amine (N,N-diisopropyl-N-ethylamine). Said two phases are liable to contain, in small amounts, side products (essentially dissolved amine for the light phase and essentially amine decomposition products for the heavy phase).

To isolate the borazane formed, present in the light phase, the process was performed as follows:

discharging, via a withdrawal cannula located at the bottom of the reactor, of the heavy phase essentially containing the amine (N,N-diisopropyl-N-ethylamine); and then evaporating the (liquid) ammonia of the light phase by depressurization of the reactor (for 15 minutes at a temperature of 20° C.).

The (solid) borazane recovered contained (liquid) amine (about 9.5% by mass). It was first suction filtered by filtration (under nitrogen, at room temperature, under a vacuum of $10^3$ Pa (10 mbar)) and then dried under vacuum in an oven (at 20° C., for 12 hours, under a reduced pressure of $10^3$ Pa (10 mbar)).

Borazane was finally obtained in a yield of 93% (the sampling performed upstream was taken into account for the calculation of this yield).

Its purity was monitored by solid $^{11}$B NMR. It was pure to 97% by mass. The main impurity it contained was boron oxides. The borazane obtained was stored under argon.

The ammonia recovered was recompressed and recycled upstream of the synthesis (for reaction with the amine-borane complex).

EXAMPLE 2

A jacketed glass reactor, with a volume of 300 ml, withstanding a pressure of $10^6$ Pa (10 bar), equipped with a magnetic stirrer, was used.

It was rendered inert beforehand with nitrogen and thermostatically regulated at 20° C.

0.665 mol of ammonia was transferred in, from an ammonia bottle (under $7\times10^5$ to $8\times10^5$ Pa (7 to 8 bar of pressure)), into said inertized and thermostatically regulated reactor.

Stirring was then started. The amine-borane complex (N,N-diisopropyl-N-ethylamine borane (commercial product); 0.013 mol) was then added in less than 30 seconds. The ammonia (liquid)/amine-borane complex mole ratio was thus greater than 51.

After 40 minutes, the stirring was stopped. To check that the reaction (N,N-diisopropyl-N-ethylamine borane+NH$_3$ (liquid)) was complete, a sample of the reaction medium (liquid) was withdrawn. The sampling (in a vial) was performed, hermetically, after placing the headspace of the internal volume of the reactor under pressure of nitrogen. The sample withdrawn, diluted in tetrahydrofuran (THF), was analyzed by $^{11}$B (boron) NMR. Absence of the amine-borane complex was confirmed. The reaction was thus complete (within the limits of detection by NMR analysis).

After stopping the stirring, the reaction medium was demixed and two phases were observed: a light phase, essentially containing the borazane (NH$_3$BH$_3$) formed in solution in liquid ammonia and a heavy phase essentially containing the amine (N,N-diisopropyl-N-ethylamine). Said two phases are liable to contain, in small amounts, side products (essentially dissolved amine for the light phase and essentially amine decomposition products for the heavy phase).

To isolate the borazane formed, present in the light phase, the process was performed as follows:

evaporating the (liquid) ammonia of said light phase by depressurization of the reactor (for 15 minutes at a temperature of 20° C.);

recovering a solid/liquid mixture mainly containing borazane and amine ((solid) borazane/(liquid)amine);

filtrating under inert gas (nitrogen) for recovery of said borazane.

The isolated borazane was then dried under vacuum, at 20° C., for 12 hours, under a reduced pressure of $10^3$ Pa (10 mbar) (for removal of the traces of amine contaminating it).

The borazane was thus obtained in a yield of 94% (the sampling performed upstream was taken into account for the calculation of this yield).

Its purity was monitored by solid $^{11}$B NMR. It was pure to 97% by mass. The main impurity it contained consisted of boron oxides (despite the inertizing with nitrogen, it is in fact virtually impossible to avoid the formation of a very small amount of boron oxide(s), quite probably due to the presence of small amounts of oxygen in the inertizing gas and/or in the liquid ammonia). The borazane obtained was stored under argon.

The ammonia recovered was recompressed and recycled upstream of the synthesis (for reaction with the amine-borane complex).

The invention claimed is:

1. A process for obtaining borazane (NH$_3$—BH$_3$), comprising:

providing a reactor, equipped with a stirring system and thermostatically regulated at a temperature between a temperature $\theta_1$ and 40° C.;

introducing anhydrous liquid ammonia (NH$_3$(l)) into said reactor;

introducing, with stirring, into said reactor containing anhydrous liquid ammonia (NH$_3$(l)), an amine borane complex of formula Am.BH$_3$ to obtain a mixture, amine Am of said complex of formula Am.BH$_3$ being soluble in anhydrous liquid ammonia only to a proportion of less than 10 g in 100 g of anhydrous liquid ammonia at 20° C., said amine borane complex of formula Am.BH$_3$ being introduced in an amount such that the mole ratio R=anhydrous liquid ammonia (NH$_3$(l))/amine borane complex of formula Am.BH$_3$ is greater than or equal to 5;

stirring the mixture to a point of depletion of said amine borane complex of formula Am.BH$_3$;

stopping the stirring and obtaining, in said reactor, two demixed phases:

a light phase constituted essentially of a solution of anhydrous liquid ammonia (NH$_3$(l)) containing borazane; and a heavy phase constituted essentially of the amine Am corresponding to the amine borane complex of formula Am.BH$_3$ introduced;

isolating said borazane and drying under vacuum thereof; said temperature $\theta_1$ being greater than or equal to the melting point of said amine borane complex of formula Am.BH$_3$.

2. The process as claimed in claim 1, wherein said anhydrous liquid ammonia (NH$_3$(l)) is introduced at a pressure of between $5\times10^5$ and $10^6$ Pa (5 and 10 bar).

3. The process as claimed in claim 1, wherein said reactor is, prior the introduction of the anhydrous liquid ammonia (NH$_3$(l)), rendered inert.

4. The process as claimed in claim 1, wherein said amine borane complex of formula Am.BH$_3$ is an alkylamine borane complex, the amine Am of which is a tertiary amine.

5. The process as claimed in claim 4, wherein said amine borane complex of formula Am.BH$_3$ is chosen from the N,N,N-triisopropylamine borane complex, the N,N-diisopropyl-N-ethylamine borane complex, and mixtures thereof.

6. The process as claimed in claim 1, wherein $5 \leq R \leq 20$.

7. The process as claimed in claim 1, wherein said reactor is thermostatically regulated between 18 and 30° C. and wherein said amine borane complex of formula $Am.BH_3$ consists of the N,N-diisopropyl-N-ethylamine borane complex.

8. The process as claimed in claim 1, wherein isolating borazane comprises:
discharging said heavy phase, constituted essentially of said amine Am;
removing by evaporation the anhydrous liquid ammonia ($NH_3(l)$) of said light phase remaining in said reactor, thereby obtaining a solid; and
suction filtrating said solid obtained.

9. The process as claimed in claim 1, wherein said isolation of borazane comprises:
removing, by evaporation, the anhydrous liquid ammonia ($NH_3(l)$) of said light phase, lying on said heavy phase, a second mixture resulting from said removal; and
filtrating said second mixture.

10. The process as claimed in claim 8, further comprising recompressing ammonia removed by evaporation.

11. The process as claimed in claim 1, further comprising, upstream, a synthesis of the amine borane complex of formula $Am.BH_3$ from diborane ($B_2H_6$) and an amine Am.

12. The process as claimed in claim 8, further comprising, upstream, a synthesis of the amine borane complex of formula $Am.BH_3$ from diborane ($B_2H_6$) and an amine Am and wherein a majority of the amine Am generated in said reactor from said amine borane complex of formula $Am.BH_3$, at least the amine Am present in said heavy phase, is recycled for performing said synthesis of the amine borane complex of formula $Am.BH_3$.

13. The process as claimed in claim 5, wherein said amine borane complex of formula $Am.BH_3$ consists of the N,N-diisopropyl-N-ethylamine borane complex.

14. The process as claimed in claim 6, wherein $8 \leq R \leq 20$.

15. The process as claimed in claim 6, wherein $8 \leq R \leq 12$.

16. The process as claimed in claim 7, wherein said reactor is thermostatically regulated between 18 and 25° C.

17. The process as claimed in claim 7, wherein said reactor is thermostatically regulated at 20° C.

18. The process as claimed in claim 9, further comprising recompressing ammonia removed by evaporation.

19. The process as claimed in claim 10, further comprising recompressing ammonia removed by evaporation and recycling thereof into said reactor.

20. The process as claimed in claim 18, further comprising recompressing ammonia removed by evaporation and recycling thereof into said reactor.

* * * * *